(12) United States Patent
Dahmen

(10) Patent No.: US 9,307,892 B2
(45) Date of Patent: Apr. 12, 2016

(54) ENDOSCOPE WITH AN ADJUSTABLE VIEWING DIRECTION

(71) Applicant: Karl Storz GmbH & Co. KG, Tuttlingen (DE)

(72) Inventor: Jan Dahmen, Tuttlingen (DE)

(73) Assignee: Karl Storz, GmbH & Co. KG, Tuttlingen (DE)

( * ) Notice: Subject to any disclaimer, the term of this patent is extended or adjusted under 35 U.S.C. 154(b) by 86 days.

(21) Appl. No.: 14/084,144

(22) Filed: Nov. 19, 2013

(65) Prior Publication Data
US 2014/0142385 A1    May 22, 2014

(30) Foreign Application Priority Data

Nov. 22, 2012   (DE) .................. 10 2012 111 290

(51) Int. Cl.
| | | |
|---|---|---|
| *A61B 1/06* | (2006.01) | |
| *A61B 1/00* | (2006.01) | |
| *A61B 1/005* | (2006.01) | |
| *A61B 1/002* | (2006.01) | |

(52) U.S. Cl.
CPC ........... *A61B 1/00183* (2013.01); *A61B 1/0052* (2013.01); *A61B 1/00055* (2013.01); *A61B 1/00066* (2013.01); *A61B 1/00071* (2013.01); *A61B 1/00158* (2013.01); *A61B 1/00165* (2013.01); *A61B 1/00179* (2013.01); *A61B 1/00181* (2013.01); *A61B 1/002* (2013.01)

(58) Field of Classification Search
USPC ................... 600/131, 137, 173–174; 359/824
See application file for complete search history.

(56) References Cited

U.S. PATENT DOCUMENTS

| | | | | |
|---|---|---|---|---|
| 3,856,000 A | * | 12/1974 | Chikama ................. | 600/173 |
| 4,846,154 A | * | 7/1989 | MacAnally et al. .......... | 600/171 |
| 5,621,830 A | * | 4/1997 | Lucey et al. .................. | 385/25 |
| 6,425,857 B1 | * | 7/2002 | Rudischhauser et al. ..... | 600/112 |
| 6,616,602 B1 | * | 9/2003 | Witte ............................ | 600/167 |
| 6,632,173 B1 | * | 10/2003 | Kehr et al. .................... | 600/167 |
| 6,638,216 B1 | * | 10/2003 | Durell .......................... | 600/173 |
| 6,641,531 B2 | * | 11/2003 | Kehr ............................. | 600/172 |
| 6,929,603 B2 | * | 8/2005 | Durell .......................... | 600/173 |
| 7,056,285 B2 | * | 6/2006 | Kehr ............................. | 600/163 |

(Continued)

FOREIGN PATENT DOCUMENTS

| | | |
|---|---|---|
| DE | 10136998 A1 | 2/2003 |
| DE | 102009049143 B3 | 12/2010 |

(Continued)

*Primary Examiner* — Matthew J Kasztejna
(74) *Attorney, Agent, or Firm* — Whitmyer IP Group LLC

(57) ABSTRACT

An endoscope with an adjustable viewing direction includes a shaft, an image transmission device for transmitting an image from a distal end of the endoscope to a proximal end of the endoscope, a hermetically tight sheath around the image transmission device, with a light admission window at the distal end of the endoscope, a manipulating device at the proximal end of the endoscope, a swivel actuation device on the manipulating device for manual adjustment of an angle between the viewing direction and a longitudinal axis of the shaft, a magnetic coupling device for magnetically transmitting a force, parallel to the longitudinal axis of the shaft, between the swivel actuation device and a force transmission device inside the hermetically tight sheath, and a rotation actuation device on the manipulating device for manually rotating the viewing direction about the longitudinal axis of the shaft relative to the manipulating device.

13 Claims, 2 Drawing Sheets

(56) References Cited

U.S. PATENT DOCUMENTS

| | | |
|---|---|---|
| 7,229,406 B2 * | 6/2007 | Kehr et al. ............... 600/172 |
| 8,343,042 B2 * | 1/2013 | Leiner et al. ............. 600/167 |
| 8,485,968 B2 * | 7/2013 | Weimer et al. ............ 600/173 |
| 8,852,086 B2 * | 10/2014 | Pauli et al. .............. 600/173 |
| 2004/0236183 A1 * | 11/2004 | Durell ..................... 600/173 |
| 2005/0004435 A1 * | 1/2005 | Kehr et al. ............... 600/172 |
| 2007/0010707 A1 * | 1/2007 | Leiner et al. ............. 600/112 |
| 2007/0112254 A1 * | 5/2007 | Weigel et al. ............ 600/137 |
| 2010/0030031 A1 | 2/2010 | Goldfarb et al. |
| 2012/0136213 A1 * | 5/2012 | Weimer et al. ............ 600/173 |

FOREIGN PATENT DOCUMENTS

| | | |
|---|---|---|
| DE | 102010040990 A1 | 3/2012 |
| DE | 102010047884 A1 | 4/2012 |
| DE | 102011012426 A1 | 8/2012 |
| EP | 0907900 B1 | 9/2003 |
| EP | 2353493 A1 | 8/2011 |
| EP | 2430970 A2 | 3/2012 |
| EP | 2430971 A2 | 3/2012 |
| WO | 9844376 A1 | 10/1998 |

* cited by examiner

ENDOSCOPE WITH AN ADJUSTABLE VIEWING DIRECTION

FIELD OF THE INVENTION

The present invention relates to an endoscope with an adjustable viewing direction and in particular to the coupling between an actuation device and the adjustment of the viewing direction.

BACKGROUND OF THE INVENTION

In addition to endoscopes with a fixed viewing direction parallel to or at an angle to the longitudinal axis of the shaft, endoscopes with an adjustable viewing direction are increasingly being used. Free adjustability of the viewing direction within a predetermined angle range can permit substantially more flexible use and can thus allow medical personnel to work more quickly, under less strain and therefore also more safely and more economically.

In order to allow an endoscope to be autoclaved and therefore to be re-used many times over for medical applications, the beam path of the endoscope has to be protected by a hermetically tight sheath against entry of moisture even at a high temperature and at an overpressure. To ensure that forces and movements generated on an actuation device outside the hermetically tight sheath can be transmitted into the interior of the hermetically tight sheath, a number of concepts were developed based on a magnetic coupling between magnets outside and inside the hermetically tight sheath.

EP 0 907 900 B1 (first published as WO 98/44376 A1) describes an endoscope with a hermetically tight sheath. A movement of an actuation device is transmitted magnetically from a ring arranged outside the sheath to a ring arranged inside the sheath. Neither the outer ring nor the inner ring is axially movable. A rotation of the inner ring is transmitted by means of a thread to an axially movable structural element.

EP 2 353 493 A1 describes a medical instrument with a magnetic actuator. One or more magnets outside and inside a hermetically tight sheath are axially movable and also rotatable about a common axis, in order to transmit axial forces and also torques by magnetic coupling. Axial forces can be transmitted for focusing or for other actions (paragraph [0019]).

EP 2 430 970 A2 and EP 2 430 971 A2 describe endoscopes with an adjustable viewing direction. A rotation movement of an actuation element is converted by means of a gear into an axial movement of a draw tube.

DE 10 2011 012 426 A1 describes an endoscopic instrument for use by one hand. An adjustment element is arranged on the outside of the instrument in such a way that it can be moved ergonomically with one finger of a hand that holds the instrument, in order to adjust a viewing direction of the endoscopic instrument (paragraphs [0009], [0036], [0051]).

SUMMARY OF THE INVENTION

It is an object of the present invention to create an improved endoscope with an adjustable viewing direction.

This object is achieved by the subjects of the independent claims. Developments are set forth in the dependent claims.

An endoscope with an adjustable viewing direction comprises a shaft, an image transmission device for transmitting an image from a distal end of the endoscope to a proximal end of the endoscope, a hermetically tight sheath around the image transmission device, with a light admission window at the distal end of the endoscope, a manipulating device at the proximal end of the endoscope, a swivel actuation device on the manipulating device for manual adjustment of an angle between the viewing direction and a longitudinal axis of the shaft, a magnetic coupling device for magnetically transmitting a force, parallel to the longitudinal axis of the shaft, between the swivel actuation device and a force transmission device inside the hermetically tight sheath, and a rotation actuation device on the manipulating device for manually rotating the viewing direction about the longitudinal axis of the shaft relative to the manipulating device.

The endoscope is in particular a medical endoscope, or an endoscope for microinvasive diagnostic and surgical interventions, or for other medical interventions. An adjustable viewing direction means a viewing direction which is not only rotatable about the longitudinal axis of the shaft of the endoscope but which is also adjustable in terms of its angle to the longitudinal axis of the shaft. The shaft of the endoscope is in particular rigid and in particular straight. The image transmission device comprises, in particular in the case of a straight and rigid shaft, a rod lens system composed of a plurality of rod lenses. In the case of a curved or curvable shaft, the image transmission device can comprise an ordered bundle of light guide fibers. Alternatively, the image transmission device can be designed for the electronic transmission of an image, in which case light issuing from an object is converted by a camera, at or near the distal end of the shaft, to an electronic signal, which represents the detected image and is transmitted to the proximal end of the endoscope.

A particular component of the hermetically tight sheath is a tube which extends from the distal end of the shaft as far as the manipulating device, and which is arranged in particular inside an outer shaft tube. In addition to this inner tube, which is part of the hermetically tight sheath, the outer shaft tube can also comprise light guides for transmitting illumination light from the proximal end to the distal end of the endoscope. Alternatively or in addition, the outer shaft tube can comprise one or more channels for receiving one or more medical instruments, for conveying a rinsing fluid, and for aspirating fluids and/or tissue fragments or other particles.

The light admission window of the hermetically tight sheath at the distal end of the endoscope is closed by a window component, which is made of an optically transparent material and which is inserted in a hermetically tight manner into the light admission window. Particularly if the image transmission device is designed for optical transmission of an image, the hermetically tight sheath also comprises a light exit window, which is closed by a corresponding window component, made of an optically transparent material, at the proximal end of the endoscope. The light admission window and, if appropriate, also the light exit window can each be of a plane or curved configuration and can also be designed as lenses or prisms.

The manipulating device has in particular the form of an ergonomically advantageously shaped grip. The swivel actuation device and the rotation actuation device are in particular arranged on the manipulating device in such a way that they can each be easily actuated by one or more fingers of a hand that grips and holds the manipulating device.

The force transmission device inside the hermetically tight sheath is designed to transmit, to the distal end of the endoscope, a force generated manually by means of the swivel actuation device and also a corresponding movement for adjusting the angle between the viewing direction and the longitudinal axis of the shaft. At the distal end of the endoscope, the force transmission device is in particular mechanically coupled to a swivelable or otherwise movable mirror or prism or another optical device for adjusting the viewing direction.

The rotation actuation device is designed in particular for the manual rotation of the image transmission device and in particular also for the manual rotation of the hermetically tight sheath about the longitudinal axis of the shaft.

The design of the magnetic coupling device for magnetically transmitting a force parallel to the longitudinal axis of the shaft may permit unexpectedly simple construction and production. This may be further helped by the fact that the rotation actuation device can be of a purely mechanical design and the magnetic coupling device can be designed merely to transmit a force between the swivel actuation device and the force transmission device.

In an endoscope of the kind described here, the force transmission device in particular is movable parallel to the longitudinal axis of the shaft and extends from the magnetic coupling device to as far as the distal end of the endoscope.

In an endoscope of the kind described here, the magnetic coupling device is in particular designed to transmit no torque.

In particular, the magnetic coupling device is designed to transmit no torque about the longitudinal axis of the shaft. For this purpose, the magnetic coupling device has in particular a magnetic field which is generated by one or more permanent magnets and which is rotationally symmetrical with respect to the longitudinal axis of the shaft.

The design of the magnetic coupling device, such that it transmits no torque, means that the force transmission device and with it in particular the image transmission device can be rotated about the longitudinal axis of the shaft without affecting the angle between the viewing direction and the longitudinal axis of the shaft. This means that a swiveling of the viewing direction (change of the angle between the viewing direction and the longitudinal axis of the shaft) and a rotation of the viewing direction about the longitudinal axis of the shaft can take place entirely independently of each other. In particular, an actuation of the swivel actuation device does not result in a rotation of the viewing direction about the longitudinal axis of the shaft, and an actuation of the rotation actuation device does not result in a change of the angle between the viewing direction and the longitudinal axis of the shaft. The endoscope can be handled in a particularly simple manner solely on account of the magnetic coupling device being designed such that it does not transmit any torque.

In an endoscope of the kind described here, the swivel actuation device is movable along a predetermined path, in particular by means of a finger of a hand that grips the manipulating device.

The swivel actuation device is in particular movable along a straight path, in particular parallel to the longitudinal axis of the shaft. The swivel actuation device is advantageously arranged ergonomically on the manipulating device. For this purpose, the swivel actuation device is arranged on the manipulating device particularly in such a way that, when the manipulating device is gripped with one hand, a finger comes to lie on the swivel actuation device easily and in a movement that does not deviate from a natural movement pattern.

In an endoscope of the kind described here, the rotation actuation device is arranged in particular at the distal end of the manipulating device.

The rotation actuation device is arranged in particular in the transition area between manipulating device and shaft. This arrangement may be ergonomically advantageous, particularly for permitting a manual rotation of the viewing direction about the longitudinal axis of the shaft by means of one or two fingers of a hand that grips and holds the manipulating device.

In an endoscope of the kind described here, the rotation actuation device is in particular connected rigidly to a proximal area of an outer shaft tube.

The rotation actuation device has in particular substantially the shape of a wheel or ring, of which the outer circumference can be grooved, profiled or otherwise configured such that actuation not only requires a force fit between the actuating fingers and the rotation actuation device, but also a form fit has to be produced easily. The design of the rotation actuation device as a wheel or ring can permit particularly intuitive control, in particular an intuitive rotation of the viewing direction about the longitudinal axis of the shaft.

An endoscope of the kind described here also comprises in particular a gear for converting a first force and a first displacement on the swivel actuation device to a second force and a second displacement on the force transmission device, wherein the force transmission device is movable parallel to the longitudinal axis of the shaft and extends from the manipulating device to as far as the distal end of the endoscope.

The gear comprises in particular one or more levers or one or more balls movable in a radial direction between conical surfaces of different gradients at the drive and output of the gear. The gear is in particular a step-down gear for converting a smaller force and a longer displacement on the swivel actuation device to a greater force and a shorter displacement on the force transmission device. The gear is in particular arranged between the magnetic coupling device and the force transmission device and is partially integrated with each of these.

The displacements of the force transmission device that are necessary for adjusting the angle between the viewing direction and the longitudinal axis of the shaft are generally short in relation to the movement that can be generated manually on an actuation device. The arrangement of a step-down gear between the swivel actuation device and the force transmission device can make it easier to obtain more sensitive manual adjustment of the angle between the viewing direction and the longitudinal axis of the shaft.

In an endoscope of the kind described here, the magnetic coupling device in particular comprises an annular component with a rotationally symmetrical inner face, of which the diameter increases continuously in a direction parallel to the longitudinal axis of the shaft, inside the hermetically tight sheath.

On the annular component inside the hermetically tight sheath, a rotationally symmetrical arrangement of one or more magnets is in particular provided, or an arrangement of one or more magnets that generate a magnetic field that is rotationally symmetrical with respect to the longitudinal axis is provided. The rotationally symmetrical inner face is in particular conical or has the shape of a jacket surface of a circular truncated cone or of another cutout of a jacket surface of a circular cone.

In an endoscope of the kind described here, the annular component is in particular movable parallel to the longitudinal axis of the shaft and is rotatable about the longitudinal axis of the shaft.

The rotatability of the annular component about the longitudinal axis of the shaft can form an alternative or additional measure to the decoupling, already described in another context, between the swiveling and the rotation of the viewing direction and can thus contribute to the intuitive and economic manipulation of the endoscope.

In an endoscope of the kind described here, a rotation of the annular component in particular causes no change of the angle between the viewing direction and the longitudinal axis of the shaft and no rotation of the viewing direction about the longitudinal axis of the shaft.

In an endoscope of the kind described here, the force transmission device is in particular tubular and surrounds the image transmission device substantially in the form of a jacket.

Deviations of the force transmission device from a tubular or cylinder-jacket-shaped (in particular circular cylinder-jacket-shaped) design can in particular lie in one or more openings or recesses. Further deviations from an ideally tubular or cylinder-jacket-shaped design lie in particular at the ends of the force transmission device. At these ends in particular, the force transmission device can be further designed so as not to surround the image transmission device in the form of a jacket.

In an endoscope of the kind described here, the force transmission device is prevented from rotating relative to the image transmission device, in particular by a device with a form fit.

The device for preventing the force transmission device from rotating relative to the image transmission device comprises in particular a pin, which engages in an oblong hole, wherein the pin can be provided on the force transmission device and the oblong hole can be provided on the image transmission device or on the hermetically tight sheath, or vice versa.

In an endoscope of the kind described here, the outer shaft tube is in particular coupled to the hermetically tight sheath.

In particular, the outer shaft tube and the hermetically tight sheath are connected mechanically rigidly to each other. The mechanically rigid connection or other form of mechanical coupling between the outer shaft tube and the hermetically tight sheath is provided in particular between the distal ends of the outer shaft tube and of the hermetically tight sheath. In this case, a space can be provided proximally from the distal ends of the outer shaft tube and hermetically tight sheath. This space can accommodate one or more light guides for transmitting illumination light and/or one or more channels for receiving medical instruments, for conveying a rinsing fluid and for aspirating fluids and particles.

In an endoscope of the kind described here, the hermetically tight sheath and the image transmission device can be connected mechanically rigidly to each other or coupled mechanically in some other way. The hermetically tight sheath and the image transmission device are in particular rigidly connected to each other at the distal end of the endoscope and/or in the area of the manipulating device. A jacket-shaped (in particular circular cylinder-jacket-shaped or other cylinder-jacket-shaped) space can be provided therebetween, in which space the force transmission device is arranged.

An endoscope of the kind described here also in particular comprises a display which can be read off from the outside and which shows the instantaneously adjusted angle between the viewing direction and the longitudinal axis of the shaft.

The display which can be read off from the outside is in particular visible from the outside and thus visually readable. The display can comprise a scale and a pointer or a window for viewing one or more numbers or other indicators of the scale.

An endoscope of the kind described here is in particular designed such that an actuation of the rotation actuation device has no effect on the adjusted angle between the viewing direction and the longitudinal axis of the shaft.

BRIEF DESCRIPTION OF THE DRAWINGS

Embodiments are explained in more detail below on the basis of the attached figures, in which.

DETAILED DESCRIPTION OF THE INVENTION

Figure 1:
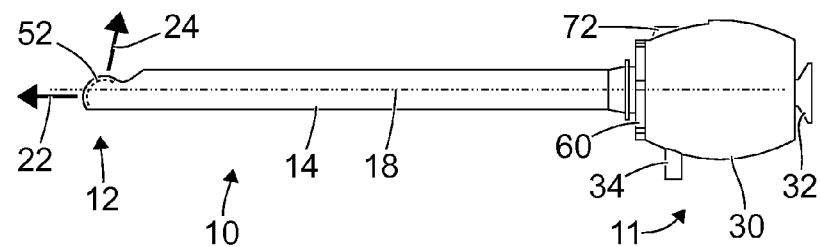
FIG. 1 shows a schematic view of an endoscope with an adjustable viewing direction.

FIG. 1 shows a schematic view of an endoscope 10 with a proximal end 11 and a distal end 12. A shaft, of which only an outer shaft tube 14 with a longitudinal axis 18 is visible, extends from the proximal end 11 to as far as the distal end 12 of the endoscope 10. At the distal end 12 of the endoscope, two extreme viewing directions 22, 24 are indicated, between which the viewing direction is adjustable (in particular steplessly).

A manipulating device 30 with an eyepiece 32, and with a coupling 34 for a light guide cable, is provided at the proximal end 11 of the endoscope 10. By way of the coupling 34, the manipulating device 30 can be coupled, via a light guide cable not shown in the figures, to a light source for providing illumination light.

A rotation actuation device 60 and a swivel actuation device 70 are also provided on the manipulating device 30. The rotation actuation device 60 is arranged in the transition area between the manipulating device 30 and the shaft 14, or at the distal end of the manipulating device 30 and at the proximal end of the shaft 14. The rotation actuation device 60 has the shape of a profiled wheel which, by means of one or more fingers of a hand that grips the manipulating device 30, can be turned about the longitudinal axis 18 of the shaft 14 in order to rotate the viewing direction of the endoscope 10 about the longitudinal axis 18 of the shaft 14. The swivel actuation device 70 is arranged on the manipulating device 30 in such a way that it can be moved, by means of one finger of a hand that grips and holds the manipulating device 30, along a path parallel to the longitudinal axis 18 of the shaft 14, in order to change the angle between the viewing direction 22, 24 and the longitudinal axis 18 of the shaft 14.

At the distal end 12 of the endoscope 10, a light admission window 52 is indicated through which light can enter the shaft 14 from an object lying in the instantaneously adjusted viewing direction 22, 24. In the following, no distinction is made between, on the one hand, the light admission window 52 or the corresponding opening and, on the other hand, the window component closing the light admission window 52 and made of an optically transparent material. The light admission window 52 has in particular the form of a cutout from the jacket of a circular cylinder, with a cylinder axis perpendicular to the plane of the drawing in FIG. 1, or the form of a cutout from a spherical surface or from a surface of an ellipsoid.

Figure 2:
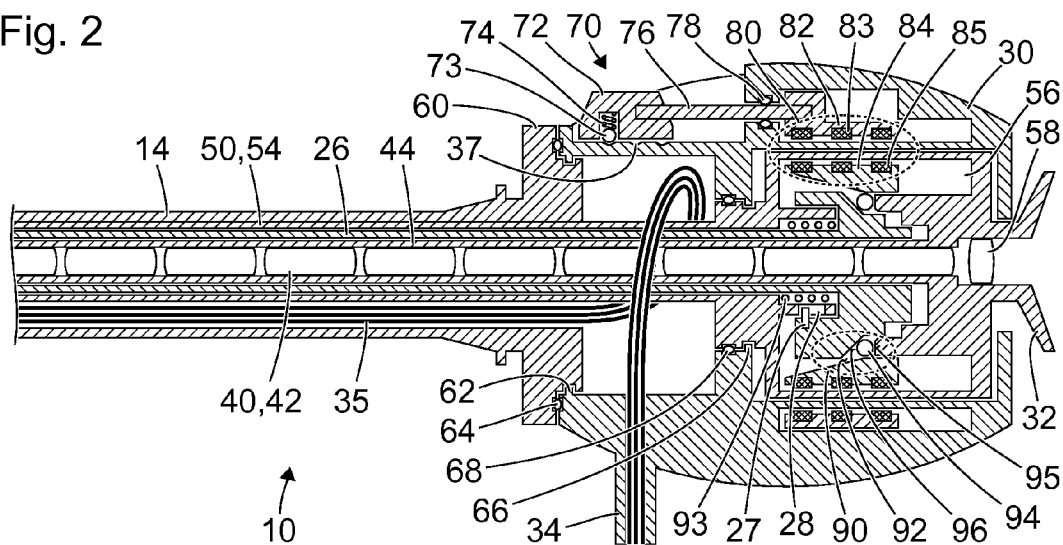
FIG. 2 shows a schematic cross-sectional view of a proximal area of an embodiment of the endoscope from FIG. 1.

FIG. 2 shows a schematic cross-sectional view of a proximal area of an embodiment of the endoscope 10 from FIG. 1.

The sectional plane in FIG. 2 is parallel to the plane of the drawing in FIG. 1 and contains the longitudinal axis 18 (cf. FIG. 1) of the shaft 14.

In the outer shaft tube 14 of the endoscope 10, an inner shaft tube 54 and a bundle of light guides 35 are arranged next to each other. The light guides 35 lead from the coupling 34 on the manipulating device 30 to the distal end 12 of the endoscope 10 (cf. FIG. 1). By means of a light guide cable (not shown in the figures), illumination light transmitted from a light source to the coupling 34 on the manipulating device 30 can be transmitted from the light guides 35 to the distal end 12 of the endoscope 10 and can emerge there and illuminate an object that is to be observed. Between the coupling 34 and the outer shaft tube 14, the light guides 35 are routed in a hollow space such that the outer shaft tube 14 can be rotated about its longitudinal axis 18 (cf. FIG. 1) relative to the manipulating device 30 within a predetermined angle range.

The inner shaft tube 54 is a component part of a hermetically tight sheath 50. The hermetically tight sheath 50 has a greatly enlarged cross section in an area inside the manipulating device 30 and it there encloses a chamber 56, which is described below. At the distal end 12 of the endoscope 10, the hermetically tight sheath 50 has the light admission window 52, described above with reference to FIG. 1, which has a window component made of an optically transparent material and hermetically closing the light admission window 52. At the proximal end 11 of the endoscope 10, the hermetically tight sheath 50 has a light exit window 58, and a window component made of an optically transparent material and hermetically sealing the light exit window 58. The light exit window 58 is designed in particular as a lens and is a component part of the eyepiece 32 or is arranged near the eyepiece 32.

The hermetically tight sheath 50 encloses or contains, particularly in the area of the inner shaft tube 54 but also in the area of the chamber 56, an image transmission device 40 with a plurality of rod lenses 42 in a system shaft 44. Moreover, the hermetically tight sheath 50 encloses an objective, or one or more lenses or mirrors, and a swivelable mirror, a swivelable prism or another optical device for adjusting the viewing direction 22, 24 (cf. FIG. 1), which are not shown in the figures, at the distal end 12 of the endoscope 10.

Between the inner shaft tube 54 and the system shaft 44 there is a space which has substantially the shape of a cylinder jacket and in which a push-and-pull tube is arranged as force transmission device 26. The force transmission device 26 is movable parallel to the longitudinal axis 18 (cf. FIG. 1) of the outer shaft tube 14. At the distal end 12 of the endoscope 10, the force transmission device 26 is mechanically coupled to said device for adjusting the viewing direction (in particular a swivelable mirror or swivelable prism). By moving the force transmission device 26 parallel to the longitudinal axis 18 of the outer shaft tube 14, the viewing direction 22, 24 of the endoscope 10 is adjusted or changed.

The rotation actuation device 60, already described above with reference to FIG. 1, is formed in one piece with the proximal end of the outer shaft tube 14 or is joined thereto with a cohesive bond, a force fit and/or a form fit. Between the rotation actuation device 60 and the manipulating device 30, there are a first, distal rotation bearing 62, which is indicated as a simple slide bearing in FIG. 2, and a first, distal seal 64. In the proximal direction from the first rotation bearing 62 and the first seal 64, and spaced apart from these in a direction parallel to the longitudinal axis 18 of the outer shaft tube 14, there are a second, proximal rotation bearing 66 and a second, proximal seal 68, which are provided between the inner shaft tube 54 rigidly connected to the outer shaft tube 14, on the one hand, and the manipulating device 30, on the other hand. The rotation bearings 62, 66 permit a rotation of the rotation actuation device 60 together with the outer shaft tube 14, the hermetically tight sheath 50 with the devices arranged therein, and the light guides 35 (if these are arranged in the area of the outer shaft tube 14), about the longitudinal axis 18 (cf. FIG. 1) of the outer shaft tube 14. The seals 64, 68 substantially or completely prevent fluids from entering and causing damage to the light guides 35.

The swivel actuation device 70, already mentioned above in connection with FIG. 1, comprises a sliding grip 72, which is arranged in a recess on the outside of the manipulating device 30 parallel to the longitudinal axis 18. The sliding grip 72 is arranged such that it can be moved parallel to the longitudinal axis 18 (cf. FIG. 1) by one finger of a hand that grips and holds the manipulating device 30.

The sliding grip 72 comprises a locking ball 73, which is pressed by a locking spring 74 against a surface of the manipulating device 30. In said surface of the manipulating device 30, a plurality of locking grooves 37 are provided into which the locking ball 73 can engage, in order to hold the sliding grip 72 in corresponding positions.

The sliding grip 72 is mechanically coupled by a push rod 76 to a magnetic coupling device 80 in the interior of the manipulating device 30, in particular rigidly connected thereto. On the push rod 76, a seal 78 is provided in order to prevent fluids from entering the interior of the manipulating device 30 and in particular from reaching the magnetic coupling device 80.

The magnetic coupling device 80 comprises an outer magnet carrier 82 with a plurality of magnets 83 outside the hermetically tight sheath 50 and in particular outside the chamber 56 enclosed by the hermetically tight sheath 50. Moreover, the magnetic coupling device 80 comprises an inner magnet carrier 84 with a plurality of magnets 85 inside the chamber 56 enclosed by the hermetically tight sheath 50. The outer magnet carrier 82 and the inner magnet carrier 84 are each substantially ring-shaped in particular. A deviation from an ideal ring shape arises on the outer magnet carrier 82 in particular as a result of the mechanical connection to the proximal end of the push rod 76. The outer magnet carrier 82 and the inner magnet carrier 84 are both movable, with little play and little friction, parallel to the longitudinal axis 18 (cf. FIG. 1).

The magnets 83 on the outer magnet carrier 82 and the magnets 85 on the inner magnet carrier 84 are each designed to generate magnetic fields that are rotationally symmetrical with respect to the longitudinal axis 18 (cf. FIG. 1). In particular, the magnets 83 on the outer magnet carrier 82 and the magnets 85 on the inner magnet carrier 84 are all circular. Alternatively, it is only the magnets 83 on the outer magnet carrier 82 or only the magnets 85 on the inner magnet carrier 84 that generate a magnetic field that is rotationally symmetrical with respect to the longitudinal axis 18. In this way, no torque can be transmitted between the magnets 83 on the outer magnet carrier 82 and the magnets 85 on the inner magnet carrier 84.

The poles of the magnets 83 on the outer magnet carrier 82 and of the magnets 85 on the inner magnet carrier 84 are such that attracting and repelling forces between the magnets 83 on the outer magnet carrier 82 on the one hand and the magnets 85 on the inner magnet carrier 84 on the other hand cause the relative arrangement of the magnet carriers 82, 84 as shown in FIG. 2. A movement of the inner magnet carrier 84 relative to the outer magnet carrier 82 in a direction parallel to the longitudinal axis 18 requires a force that rises sharply as the excursion increases. However, since the outer magnet carrier 82 outside the hermetically tight sheath 50 and also the inner magnet carrier 84 inside the chamber 56 in the hermetically tight sheath 50 bear with little play and little friction, the outer magnet carrier 82 and the inner magnet carrier 84 can be jointly moved parallel to the longitudinal axis 18. In particular, a manually applied movement of the sliding grip 72 by way of the push rod 76 causes a corresponding movement of the outer magnet carrier 82 and, because of the magnetic coupling between the magnets 83 on the outer magnet carrier 82 and the magnets 85 on the inner magnet carrier 84, a corresponding movement of the inner magnet carrier 84.

The inner magnet carrier 84 is at the same time a component part of a gear 90 for converting, in particular stepping down, a movement of the swivel actuation device 70 and of the magnetic coupling device 80 on the one hand into a movement of the force transmission device 26 on the other hand, wherein the acting forces and the paths traveled on the swivel actuation device 70 and the magnetic coupling device 80 differ from those on the force transmission device 26.

The gear 90 comprises an internal cone 92 on the inner magnet carrier 84, an external cone 96 at the proximal end of the force transmission device 26, balls 94 between the internal cone 92 on the inner magnet carrier 84 and the external cone 96 on the force transmission device 26, a guide 95 for the balls 94, and a compression spring 93 between the hermetically tight sheath 50 on the one hand and the force transmission device 26 on the other hand.

The internal cone 92 on the inner magnet carrier 84 and the external cone 96 at the proximal end of the force transmission device 26 each have a constant gradient and the shape of an annular cutout from the jacket of a cone. The gradients or the opening angles of the internal cone 92 on the inner magnet carrier 84 and of the external cone 96 at the proximal end of the force transmission device 26 differ from each other. The guide 95 for the balls 94 is formed by an annular and plane contact face perpendicular to the longitudinal axis 18 of the outer shaft tube 14 (cf. FIG. 1). The compression spring 93 pushes the force transmission device 26 in the proximal direction, such that the external cone 96 at the proximal end of the force transmission device 26 bears at all times on the balls 94, and the balls 94 bear on the guide 95 and on the internal cone 92 on the inner magnet carrier 84.

Figure 3:
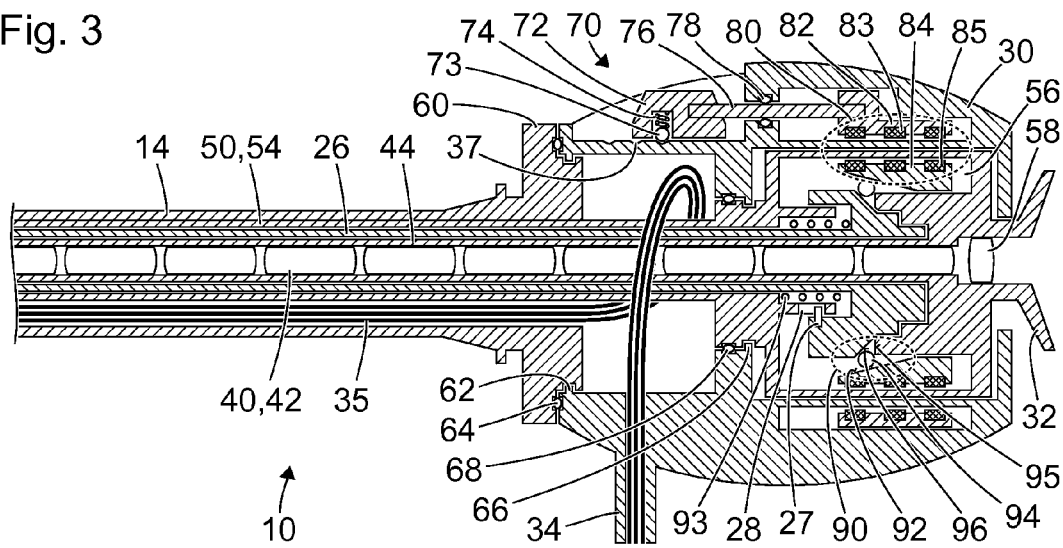
FIG. 3 shows another schematic cross-sectional view of the proximal area of the embodiment from FIG. 2.

A movement of the inner magnet carrier 84 in a direction parallel to the longitudinal axis 18 (cf. FIG. 1) of the outer shaft tube 14 causes a movement of the balls 94 in a radial direction along the guide 95 and a movement of the force transmission device 26 in a direction parallel to the longitudinal axis 18 of the outer shaft tube 14. FIG. 3 shows another schematic cross-sectional view of the proximal area of the embodiment of the endoscope 10 shown in FIG. 2, in a further configuration or situation. The swivel actuation device 70, the magnetic coupling device 80 and with it the internal cone 92 on the inner magnet carrier 84, on the one hand, and the force transmission device 26, on the other hand, are each located, in the situation shown in FIG. 2, in a distal position and, in the situation shown in FIG. 3, in a proximal position.

The different gradients or opening angles of the internal cone 92 on the inner magnet carrier 84 on the one hand and of the external cone 96 at the proximal end of the force transmission device 26 on the other hand cause a step-down or conversion of a longer displacement on the swivel actuation device 70 and on the magnetic coupling device 80 on the one hand to a shorter displacement on the force transmission device 26 on the other hand. Accordingly, a smaller force on the swivel actuation device 70 and on the magnetic coupling device 80 on the one hand is converted to a greater force on the force transmission device 26.

In a departure from the view shown in FIGS. 2 and 3, the surface at the proximal end of the force transmission device 26 and/or the surface on the inner magnet carrier 84 on which the balls 94 lie can have a non-conical shape or can have a gradient varying in a direction parallel to the longitudinal axis 18 (cf. FIG. 1) of the outer shaft tube 14. Moreover, in a departure from the view in FIGS. 2 and 3, the guide 95 for the balls 94 may not be plane and is instead curved (for example conically). In this way, a step-down ratio can be obtained that varies along the displacement.

At the proximal end of the force transmission device 26, a guide pin 27 is provided which engages in a guide slit 28. The guide slit 28 is rigidly connected to the hermetically tight sheath 50 and via the latter to the image transmission device 40. The guide pin 27 is guided movably in the guide slit 28, with little play and little friction, in a direction parallel to the longitudinal axis (cf. FIG. 1) of the outer shaft tube 14. The guide pin 27 and the guide slit 28 form a device which provides a form-fit preventing the force transmission device 26 from rotating relative to the image transmission device 40. This device protects the mechanical coupling, between the force transmission device 26 and a swivelable mirror or prism or another device determining the viewing direction 22, 24 (cf. FIG. 1) at the distal end 12 of the endoscope 10, from torsional stress.

When the rotation actuation device 60 is used to manually rotate the outer shaft tube 14 together with the hermetically tight sheath 50, the force transmission device 26 and the image transmission device 40 about the longitudinal axis 18 (cf. FIG. 1) of the outer shaft tube 14, the external cone 96 at the proximal end of the force transmission device 26 and the guide 95 are rotated relative to the outer magnet carrier 82. The described configuration of the magnets 83 on the outer magnet carrier 82 and of the magnets 85 on the inner magnet carrier 84, namely such that the generated magnetic fields are rotationally symmetrical with respect to the longitudinal axis 18 of the outer shaft tube 14, prevents a torque that inhibits or obstructs the rotation. Alternatively or in addition, this inhibiting or obstructing torque can be avoided by a free rotatability of the inner magnet carrier 84 about the longitudinal axis 18 of the outer shaft tube 14 (except for mechanical friction between external cone 96, balls 94, guide 95 and internal cone 82). This means that a change of the angle between the viewing direction 22, 24 and the longitudinal axis 18 of the outer shaft tube 14 by means of the swivel actuation device 70, on the one hand, and a rotation of the viewing direction 22, 24 about the longitudinal axis 18 of the outer tube 14 by means of the rotation actuation device 60, on the other hand, can take place independently of each other and without influencing each other.

In the embodiment in FIGS. 2 and 3, therefore, a number of measures are implemented which permit a free rotatability of the outer shaft tube 14 with the hermetically tight sheath 50 and the image transmission device 40, on the one hand, relative to the manipulating device 30, on the other hand, without affecting the angle between the viewing direction 22, 24 (cf. FIG. 1) and the longitudinal axis 18 of the outer shaft tube 14. Alternatively, only one or two of the measures may be implemented, i.e. either the rotation symmetry of the magnetic field generated by the magnets 83 on the outer magnet carrier 82 or the rotation symmetry of the magnetic field generated by the magnets 85 on the inner magnet carrier 84, or the rotation symmetry of the internal cone 92 on the inner magnet carrier 84, the guide 95 and the external cone 96 at the proximal end of the force transmission device 26.

Figure 4:
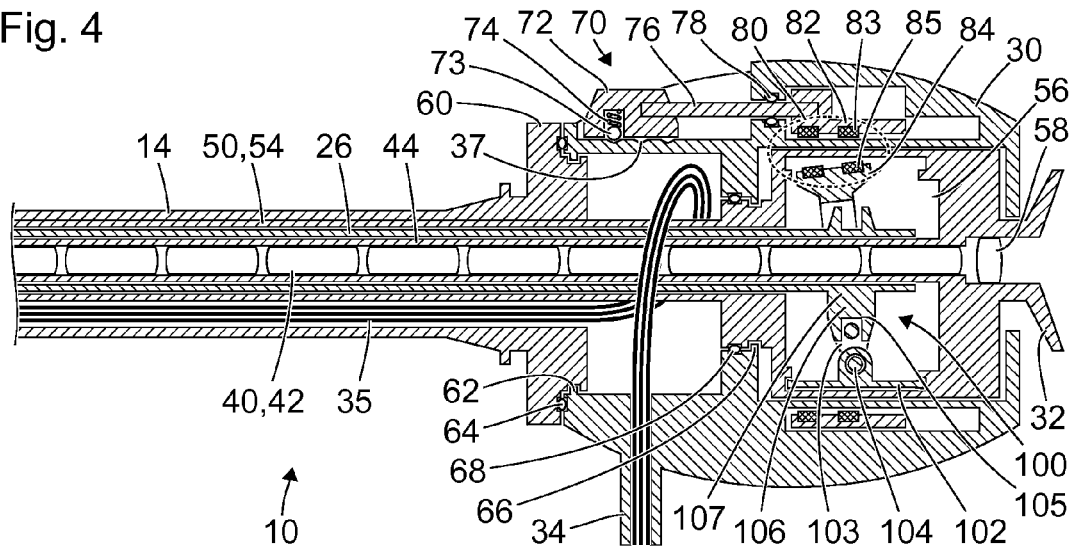
FIG. 4 shows a schematic cross-sectional view of a proximal area of another embodiment of the endoscope from FIG. 1.

FIG. 4 shows a schematic cross-sectional view of a proximal area of another embodiment of the endoscope 10 from FIG. 1. The nature of the view and in particular the sectional plane parallel to the longitudinal axis 18 (cf. FIG. 1) of the outer shaft tube 14 correspond to those of the views in FIGS. 2 and 3. The embodiment in FIG. 4 is similar in some features, properties and functions to the embodiments in FIGS. 2 and 3. Only those features, properties and functions are discussed below in terms of which the embodiment in FIG. 4 differs from the embodiments in FIGS. 2 and 3.

The embodiment in FIG. 4 differs from the embodiment in FIGS. 2 and 3 particularly in that, instead of a gear with balls between an internal cone and an external cone with different gradients, a gear 100 with a lever 103 is provided. The lever 103 is coupled to a carriage 102 by means of a swivel hinge 104. The carriage 102 is arranged in the chamber 56 inside the hermetically tight sheath 50 and is freely rotatable about the longitudinal axis 18 (cf. FIG. 1) of the outer shaft tube 14 with little play and little friction and with a form fit. The swivel hinge 104 defines a swivel axis, which is perpendicular to the longitudinal axis 18 of the outer shaft tube 14 and, in the position of the carriage 102 shown in FIG. 4, is perpendicular to the sectional plane of FIG. 4.

At the end directed away from the swivel hinge 104, the lever 103 has an inner magnet carrier 84 with a plurality of magnets 85. In contrast to the embodiment in FIGS. 2 and 3, the inner magnet carrier 84 is not movable parallel to the longitudinal axis 18 of the outer shaft tube 14, and instead it is able to swivel about the swivel axis defined by the swivel hinge 104. The magnets 83 on the outer magnet carrier 82 and the magnets 85 on the inner magnet carrier 84 are arranged and designed, in particular polarized, in such a way that each linear translational movement of the outer magnet carrier 82 causes a corresponding swiveling movement of the inner magnet carrier 84 and therefore of the lever 103 about the swivel axis defined by the swivel hinge 104.

The lever 103 has an opening 105, in which the proximal end of the force transmission device 26 engages. In particular, the lever 103 encloses the opening 105 in the manner of a frame. Inside the opening 105, a pin 106 is provided parallel to the swivel axis defined by the swivel hinge 104. The pin 106 engages in a peripheral groove 107 on the force transmission device 26. The pin 106 on the lever 103 and the peripheral groove 107 on the force transmission device 26 are designed such they permit a form-fit mechanical coupling, with little play and little friction, of the lever 103 to the force transmission device 26 for forces parallel to the longitudinal axis 18 (cf. FIG. 1) of the outer shaft tube 14 and at the same time do not inhibit or obstruct a rotation of the lever 103 (together with the carriage 102) about the longitudinal axis 18 of the outer shaft tube 14 relative to the force transmission device 26.

In a departure from the view in FIG. 4, and in a manner similar to the embodiment in FIGS. 2 and 3, a guide pin in a guide slit, or another device, can be provided which gives a form fit and prevents the force transmission device 26 from rotating relative to the image transmission device 40.

A movement of the swivel actuation device 70 and, by way of the push rod 76, of the magnetic coupling device 80 causes a corresponding swiveling movement 103 and, byway of the form-fit coupling between the pin 106 on the lever 103 and the peripheral groove 107 on the force transmission device 26, a movement of the force transmission device 26 parallel to the longitudinal axis 18 (cf. FIG. 1) of the outer shaft tube 14.

Figure 5:
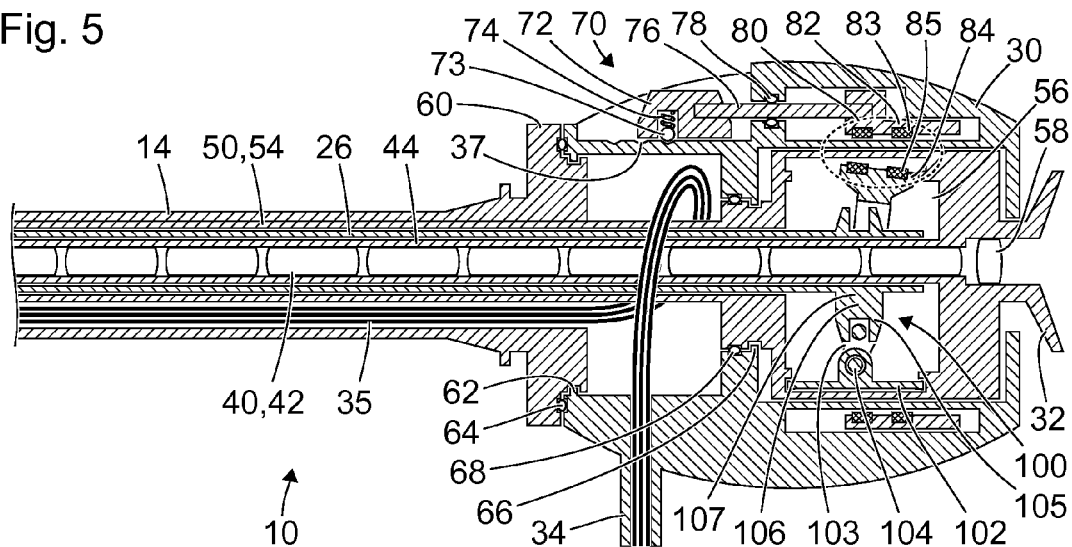
FIG. 5 shows another schematic cross-sectional view of the proximal area of the embodiment from FIG. 4.

FIG. 5 shows another schematic view of the proximal area of the embodiment of the endoscope 10 from FIG. 4. The nature of the view and in particular the sectional plane correspond to those in FIGS. 2 to 4. The situation shown in FIG. 5 differs from the one shown in FIG. 4 in that the swivel actuation device 70 and the magnetic coupling device 80 and with these, by means of the gear 100, also the force transmission device 26 are moved in the proximal direction.

The ratio of the distance of the pin 106 from the swivel axis defined by the swivel hinge 104 and of the distance of the magnetic coupling device 80 from the swivel axis defined by the swivel hinge 104 causes a corresponding step-down or conversion of a longer displacement and a smaller force on the swivel actuation device 70 and on the magnetic coupling device 80 to a shorter displacement and a greater force on the force transmission device 26.

The magnets 83 on the outer magnet carrier 82 are in particular arranged and polarized in such a way that they generate a magnetic field that is rotationally symmetrical with respect to the longitudinal axis 18 (cf. FIG. 1) of the outer shaft tube 14. This configuration prevents a torque that causes, inhibits or obstructs a rotation of the lever 103 (together with the carriage 102) about the longitudinal axis 18. An inhibiting or obstructing torque of this kind can additionally be avoided by the described free rotatability of the lever 103 together with the inner magnet carrier 84 and the carriage 102 about the longitudinal axis 18 of the outer shaft tube 14 (except for friction between carriage 102 and hermetically tight sheath 50). This means that a change of the angle between the viewing direction 22, 24 and the longitudinal axis 18 of the outer shaft tube 14 by means of the swivel actuation device 70, on the one hand, and a rotation of the viewing direction 22, 24 about the longitudinal axis 18 of the outer shaft tube 14 by means of the rotation actuation device 60, on the other hand, can take place independently of each other and without influencing each other.

In the embodiment in FIGS. 4 and 5, therefore, two measures are implemented which permit free rotatability of the outer shaft tube 14 with the hermetically tight sheath 50 and the image transmission device 40, on the one hand, relative to the manipulating device 30, on the other hand, without affecting the angle between the viewing direction 22, 24 (cf. FIG. 1) and the longitudinal axis 18 of the outer shaft tube 14. Alternatively, only one of the two measures may be implemented, i.e. either the rotation symmetry of the magnetic field generated by the magnets 83 on the outer magnet carrier 82 or the rotatability of the lever 103 with the carriage 102 about the longitudinal axis 18.

In the endoscope 10 shown in FIG. 1, and in particular in each of the embodiments shown in FIGS. 2 to 5, a display (not shown in the figures) can be provided to show the instantaneously adjusted angle. In particular, a scale is provided on an outer surface of the manipulating device 30 and has numbers or other symbols indicating the value of the angle between the viewing direction 22, 24 (cf. FIG. 1) and the longitudinal axis 18 of the outer shaft tube 14, and a pointer, which points to the scale, is provided on the sliding grip 72 or is mechanically coupled thereto. Alternatively, a window can be provided on the sliding grip 72 or can be mechanically coupled thereto and highlights a value or a symbol on the scale. Alternatively, the scale can be provided on the sliding grip 72 or mechanically coupled thereto, and the pointer, the window or another device for visible highlighting can be provided on the housing of the manipulating device 30.

The invention claimed is:

1. An endoscope with an adjustable viewing direction, comprising:
   a shaft;
   an image transmission device for transmitting an image from a distal end of the endoscope to a proximal end of the endoscope;

a hermetically tight sheath around the image transmission device, with a light admission window at the distal end of the endoscope and a light exit window at the proximal end of the endoscope, wherein the light admission window has an optically transparent window component that hermetically seals the light admission window, and the light exit window has an optically transparent window component that hermetically seals the light exit window;

a manipulating device at the proximal end of the endoscope;

a swivel actuation device on the manipulating device, for manual adjustment of an angle between the viewing direction and a longitudinal axis of the shaft;

a magnetic coupling device for magnetically transmitting a force, parallel to the longitudinal axis of the shaft, between the swivel actuation device and a force transmission device inside the hermetically tight sheath, in which the magnetic coupling device comprises an annular component with a rotationally symmetrical inner face, of which the diameter increases continuously in a direction parallel to the longitudinal axis of the shaft, inside the hermetically tight sheath; and a rotation actuation device on the manipulating device, for manually rotating the viewing direction about the longitudinal axis of the shaft relative to the manipulating device;

wherein a first portion of the hermetically tight sheath disposed inside the manipulating device has a first cross-sectional area, a second portion of the hermetically tight sheath proximate the distal end of the endoscope has a second cross-sectional area, and the first cross-sectional area is larger than the second cross-sectional area.

2. The endoscope according to claim 1, in which the magnetic coupling device is designed to transmit no torque.

3. The endoscope according to claim 1, in which the rotation actuation device is arranged at the distal end of the manipulating device.

4. The endoscope according to claim 1, in which the rotation actuation device is connected rigidly to a proximal area of an outer shaft tube.

5. The endoscope according to claim 1, further comprising:
a gear for converting a first force and a first displacement on the swivel actuation device to a second force and a second displacement on the force transmission device, wherein the force transmission device is movable parallel to the longitudinal axis of the shaft and extends from the manipulating device to as far as the distal end of the endoscope.

6. The endoscope according to claim 1, in which the annular component is movable parallel to the longitudinal axis of the shaft and is rotatable about the longitudinal axis of the shaft.

7. The endoscope according to claim 1, in which the force transmission device is tubular and surrounds the image transmission device substantially in the form of a jacket.

8. The endoscope according to claim 7, in which the force transmission device is prevented from rotating relative to the image transmission device by a device with a form fit.

9. The endoscope according to claim 8, in which an outer shaft tube is coupled to the hermetically tight sheath.

10. The endoscope according to claim 8, wherein the endoscope is designed such that an actuation of the rotation actuation device has no effect on the adjusted angle between the viewing direction and the longitudinal axis of the shaft.

11. An endoscope with an adjustable viewing direction, comprising:
a shaft;
an image transmission device for transmitting an image from a distal end of the endoscope to a proximal end of the endoscope;
a sheath around the image transmission device, with a light admission window at the distal end of the endoscope and a light exit window at the proximal end of the endoscope, wherein the light admission window has an optically transparent window component that seals the light admission window, and the light exit window has an optically transparent window component that seals the light exit window;
a manipulating device at the proximal end of the endoscope;
a swivel actuation device on the manipulating device, for manual adjustment of an angle between the viewing direction and a longitudinal axis of the shaft;
a magnetic coupling device for magnetically transmitting a force, parallel to the longitudinal axis of the shaft, between the swivel actuation device and a force transmission device inside the sheath, in which the magnetic coupling device comprises an annular component with a rotationally symmetrical inner face, of which the diameter increases continuously in a direction parallel to the longitudinal axis of the shaft, inside the hermetically tight sheath; and
a rotation actuation device on the manipulating device, for manually rotating the viewing direction about the longitudinal axis of the shaft relative to the manipulating device.

12. The endoscope according to claim 11, wherein a first portion of the sheath disposed inside the manipulating device has a first cross-sectional area, a second portion of the sheath proximate the distal end of the endoscope has a second cross-sectional area, and the first cross-sectional area is gr qtly larger than the second cross-sectional area.

13. The endoscope according to claim 11, wherein the sheath is a hermetically tight sheath.

* * * * *